(12) United States Patent  (10) Patent No.: US 9,138,338 B2
Chambers et al.  (45) Date of Patent: Sep. 22, 2015

(54) TWO-STAGE METHOD OF COMPRESSING A STENT

(75) Inventors: Sean D. Chambers, Bloomington, IN (US); Mark A. Magnuson, Bloomington, IN (US); Fred T. Parker, Unionville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 750 days.

(21) Appl. No.: 13/322,091

(22) PCT Filed: May 21, 2010

(86) PCT No.: PCT/US2010/035750
§ 371 (c)(1),
(2), (4) Date: Nov. 22, 2011

(87) PCT Pub. No.: WO2010/138411
PCT Pub. Date: Dec. 2, 2010

(65) Prior Publication Data
US 2012/0060348 A1   Mar. 15, 2012

Related U.S. Application Data

(60) Provisional application No. 61/181,093, filed on May 26, 2009.

(51) Int. Cl.
B23P 11/00 (2006.01)
A61F 2/95 (2013.01)
A61F 2/958 (2013.01)

(52) U.S. Cl.
CPC . *A61F 2/95* (2013.01); *A61F 2/958* (2013.01); *A61F 2002/9522* (2013.01); *Y10T 29/49908* (2015.01)

(58) Field of Classification Search
CPC ................. A61M 2025/1027; A61M 25/0009
USPC ............... 29/508, 515, 516, 517; 228/173.4; 72/370.07, 370.24, 370.25
See application file for complete search history.

(56) References Cited

U.S. PATENT DOCUMENTS 5,306,294 A  4/1994  Winston et al.
5,911,752 A  6/1999  Dustrude et al.
(Continued)

FOREIGN PATENT DOCUMENTS

DE         298 08 141 U1   12/1998
WO    WO 2006/117016 A1    11/2006
WO    WO 2007/081940 A2     7/2007

OTHER PUBLICATIONS

International Preliminary Report on Patentability for International Application No. PCT/US2010/035750 dated Dec. 8, 2011, 7 pages.
(Continued)

*Primary Examiner* — David Bryant
*Assistant Examiner* — Steven A Maynard
(74) *Attorney, Agent, or Firm* — Brinks Gilson & Lione

(57) ABSTRACT

A two-stage method of compressing a stent entails providing an expandable stent (100,105) in a radially expanded state. An outward pressure is applied to an inner surface of the tubular framework to support the stent, and a diameter of the stent is reduced to a first compressed diameter (D1) while applying the outward pressure. The outward pressure is halted after reaching the first compressed diameter. According to an embodiment in which the stent is balloon-expandable, a delivery balloon catheter (130) comprising an uninflated balloon in a delivery configuration is inserted into the lumen after halting the outward pressure. The diameter of the stent is reduced to a second compressed diameter (D2) smaller than the first compressed diameter to crimp the stent onto the delivery balloon catheter.

16 Claims, 7 Drawing Sheets

(56) References Cited

U.S. PATENT DOCUMENTS

| | | |
|---|---|---|
| 6,352,547 B1 | 3/2002 | Brown et al. |
| 6,745,445 B2 | 6/2004 | Spilka |
| 6,769,161 B2 | 8/2004 | Brown et al. |
| 6,863,683 B2 * | 3/2005 | Schwager et al. ............ 623/1.11 |
| 7,225,518 B2 * | 6/2007 | Eidenschink et al. ........ 29/283.5 |
| 7,343,659 B2 | 3/2008 | Weber et al. |
| 7,526,849 B2 * | 5/2009 | Serrano ............................ 29/508 |
| 8,046,897 B2 * | 11/2011 | Wang et al. ...................... 29/515 |
| 8,333,000 B2 * | 12/2012 | Huang et al. ..................... 29/282 |
| 2003/0225445 A1 | 12/2003 | Derus et al. |
| 2005/0143752 A1 | 6/2005 | Schwager et al. |
| 2007/0006441 A1 | 1/2007 | McNiven et al. |
| 2007/0270937 A1 | 11/2007 | Leanna |
| 2007/0289117 A1 * | 12/2007 | Huang et al. ..................... 29/508 |
| 2008/0016668 A1 | 1/2008 | Huang et al. |
| 2008/0028594 A1 * | 2/2008 | Lafont et al. ..................... 29/516 |
| 2008/0173061 A1 | 7/2008 | Perreault et al. |
| 2009/0088829 A1 * | 4/2009 | Wang et al. .................. 623/1.11 |

OTHER PUBLICATIONS

International Search Report and Written Opinion for International Application No. PCT/US2010/035750 dated Jul. 23, 2010, 13 pages.

* cited by examiner

TWO-STAGE METHOD OF COMPRESSING A STENT

RELATED APPLICATIONS

The present patent document is the national stage of International Patent Application PCT/US2010/035750, filed on May 21, 2010, which claims the benefit of the filing date under 35 U.S.C. 119(e) of U.S. Provisional Patent Application Ser. No. 61/181,093, filed on May 26, 2009, both of which are hereby incorporated by reference in their entirety.

TECHNICAL FIELD

The present disclosure is directed generally to expandable stents. More particularly, the present disclosure describes a two-stage method of compressing an expandable stent for securement onto or within a delivery system.

BACKGROUND

Stents are generally designed as tubular support structures that can be used in a variety of medical procedures to treat blockages, occlusions, narrowing ailments and other problems that restrict flow through body vessels. An expandable stent is radially compressed to a low-profile configuration for passage through a body vessel, and then, once in position at a treatment site, the stent may be radially expanded to a larger-diameter deployment configuration to contact and support the inner wall of the vessel. Such stents are generally classified as either balloon-expandable or self-expanding and include a framework of interconnected struts. Balloon-expandable stents expand in response to the inflation of a balloon, while self-expanding stents expand spontaneously when released from constraint, such as from a delivery device.

Balloon-expandable stents may provide the benefits of high radial stiffness and strength, minimal recoil, and controlled behavior during expansion. Prior to insertion into a body vessel, a balloon-expandable stent is compressed, such as by crimping, over an uninflated balloon catheter in order to secure the stent to the balloon in a low-profile configuration. For example, compressing or crimping may be done with a handheld tool or by way of a manual or automatic crimping device.

For some applications, it may be advantageous to provide the balloon-expandable stent with a covering or a coating prior to crimping onto the balloon catheter. Such a coating may take the form of a thin biocompatible polymer layer that overlies, underlies and/or encapsulates struts of the stent.

Generally, an uncoated stent is expanded to some fraction of its maximum expanded diameter for application of the covering to minimize the elastic expansion of the coating material that occurs during deployment and expansion of the stent. Covering of the stent can occur by various methods, such as dipping the expanded, uncoated stent into a polymer solution or attaching a thin film, sheet, or tubular structure of material to the expanded uncoated stent. Other processes, such as spray coating or electrospinning, can also be utilized depending on the covering material and the desired morphology of the final covering. After application of the coating, the covered stent may be crimped onto a balloon catheter in preparation for delivery into a body vessel.

Problems may arise during crimping of the covered stent, however, particularly if the stent was expanded to its maximum design diameter prior to the covering process. Crimping a balloon expandable stent after being deformed to an expanded state may result in instabilities during the crimping process that can lead to misalignments or bending of the struts of the crimped stent.

BRIEF SUMMARY

An improved two-stage method of radially compressing or crimping an expandable stent in preparation for delivery into a body vessel is described. The method may be particularly advantageous for covered balloon-expandable stents that have undergone an expansion process to apply the covering prior to crimping. The method may also be advantageously employed with self-expanding stents that have been radially expanded for heat-setting prior to being compressed to a low-profile state for delivery. Using the improved two-stage compression method, such expandable stents may be compressed from a radially expanded state without misalignments or bending of the struts.

The two-stage method entails a first compressing or pre-crimping step and a second compressing or crimping step. According to one embodiment, a balloon-expandable stent comprising a thin-walled tubular framework of interconnected struts is provided, where the tubular framework defines a lumen. The balloon-expandable stent may be provided in a radially expanded state. The diameter of the stent is reduced to a first compressed diameter while an outward pressure is applied to an inner surface of the tubular framework to support the stent. The outward pressure is halted after reaching the first compressed diameter. A delivery balloon catheter comprising an uninflated balloon in a delivery configuration is inserted into the lumen after halting the outward pressure. The diameter of the stent is then reduced to a second compressed diameter smaller than the first compressed diameter to crimp the stent onto the delivery balloon catheter to achieve a desired low profile and firm securement of the stent to the delivery balloon catheter.

According to another embodiment, the method entails providing a self-expanding stent comprising a thin-walled tubular framework of interconnected struts, where the tubular framework defines a lumen, and reducing a diameter of the stent to a first compressed diameter while applying an outward pressure to an inner surface of the tubular framework to support the stent. The outward pressure is halted after reaching the first compressed diameter, and the diameter of the stent is reduced to a second compressed diameter smaller than the first compressed diameter. The stent is then transferred into a restraining member, such as a sheath, which is sized to receive the stent having the second compressed diameter.

DETAILED DESCRIPTION

The improved, two-stage crimping or compression method described here is particularly advantageous for expandable stents (e.g., covered balloon-expandable stents and self-expanding stents) that have undergone an expansion process prior to crimping. Covered stents, for example, which comprise a framework of struts and covering or coating thereon, are commonly expanded during fabrication to apply the coating. Using the improved crimping method, such stents may be crimped from a radially expanded state without misalignments or misorientation of the struts, as may occur during traditional unsupported crimping processes.

FIGS. 1A-1E show exemplary steps of crimping a balloon-expandable stent 100 onto a delivery balloon catheter 130 for delivery into a body vessel. The process involves compression in two stages: (1) a supported first stage, as shown schematically in FIGS. 1B-1C, where a radially directed outward pressure is exerted against an inner surface of the stent 100 to support the stent 100 during crimping to a first compressed diameter $D_1$; and (2) an unsupported second stage, as shown schematically in FIGS. 1E-1F, where the stent 100 is crimped without support from the first compressed diameter $D_1$ to a second compressed diameter $D_2$ to secure the stent 100 to the delivery balloon catheter 130. FIGS. 2A-2E show an embodiment where the outward pressure used to support the stent 100 during the first stage is provided by an inflatable body 120. FIGS. 3A-3E show an embodiment where the outward pressure used to support the stent 100 during the first stage of crimping is provided by a mechanically expandable apparatus 300, as will be discussed further below.

Figure 4A:
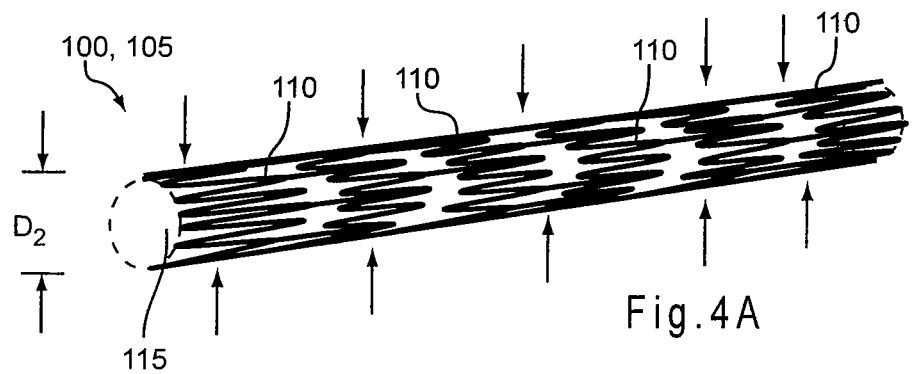
FIGS. 4A-4B show an alternative embodiment of the unsupported second stage of the method for self-expanding stents.
Figure 4B:
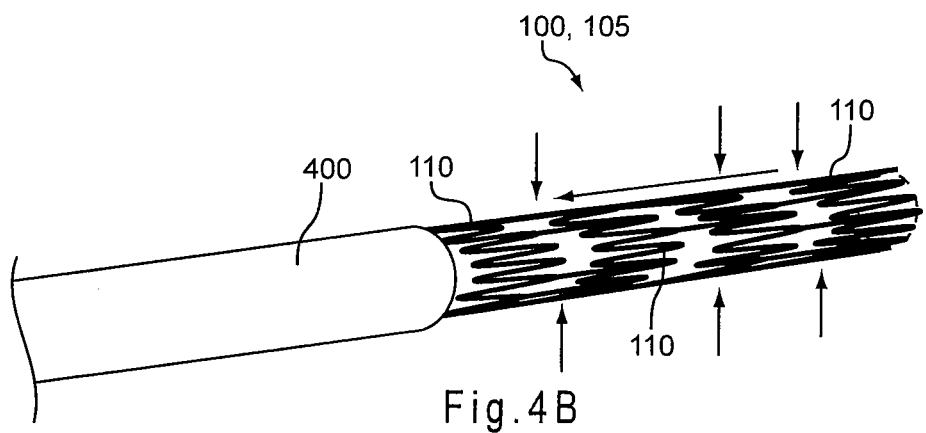

FIGS. 4A-4B, which are also discussed further below, show exemplary steps for the second stage of the crimping or compression process when the stent being compressed is a self-expanding stent instead of a balloon-expandable stent. The steps corresponding to the first stage of the process, as shown for example in FIG. 1B-1C or 2B-2C, are generic to both balloon-expandable stents and self-expanding stents.

Figure 1A:
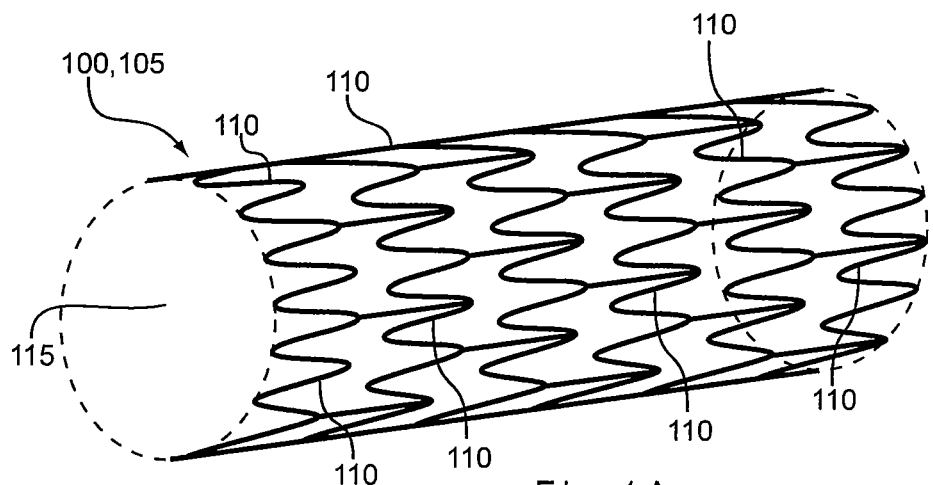
FIGS. 1A-1F show exemplary steps of a method to crimp a balloon-expandable stent onto a balloon catheter for delivery into a body vessel, where the method includes a supported first stage and an unsupported second stage.
Figure 1B:
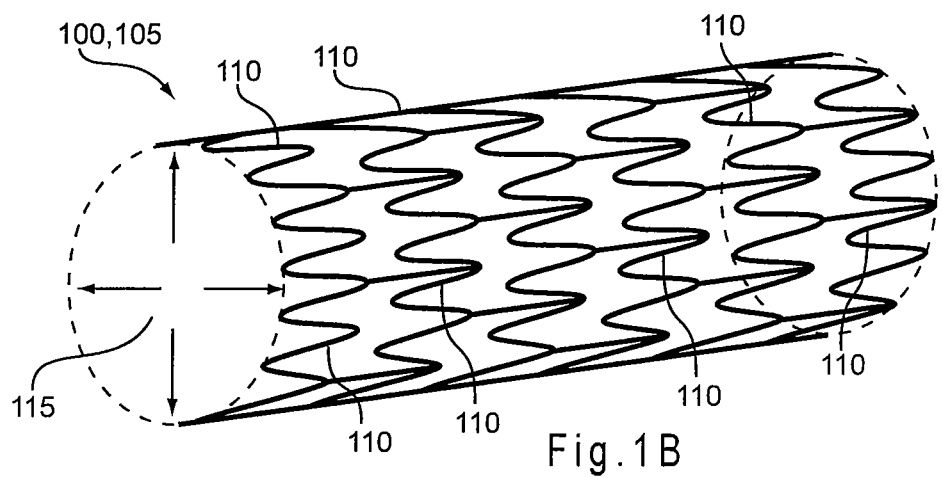
Figure 1C:
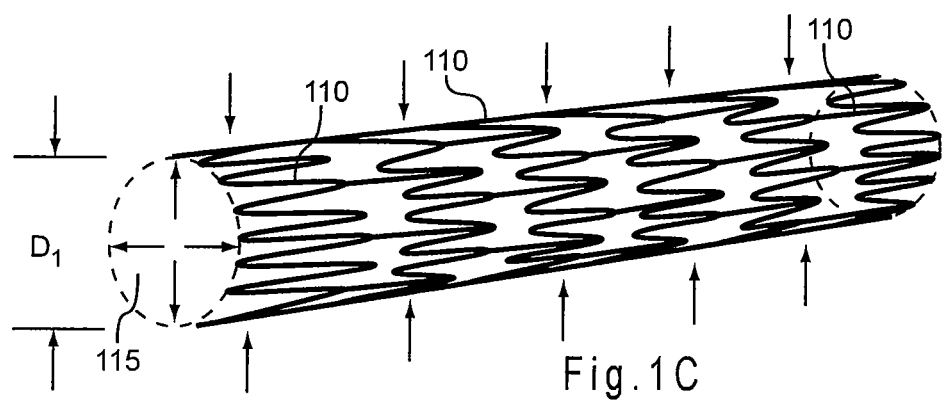
Figure 1D:
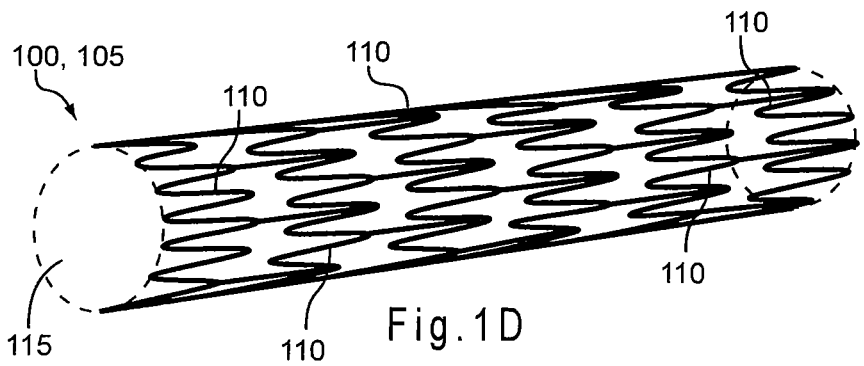
Figure 1E:
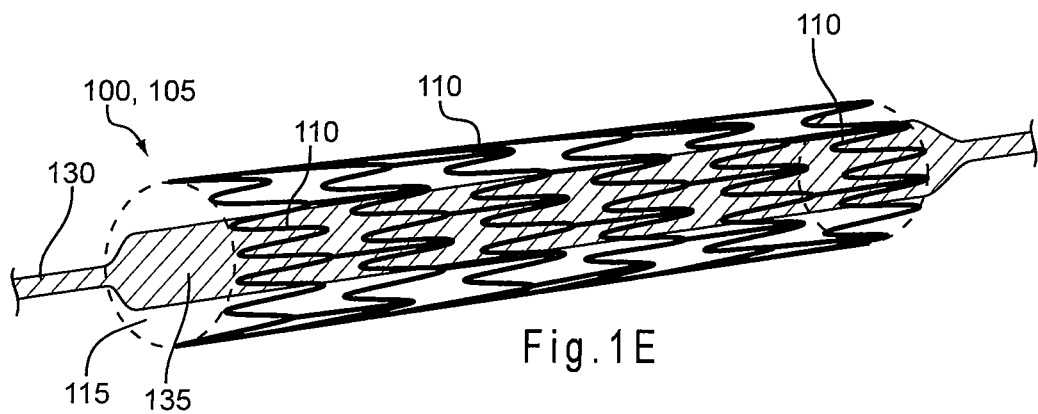
Figure 1F:
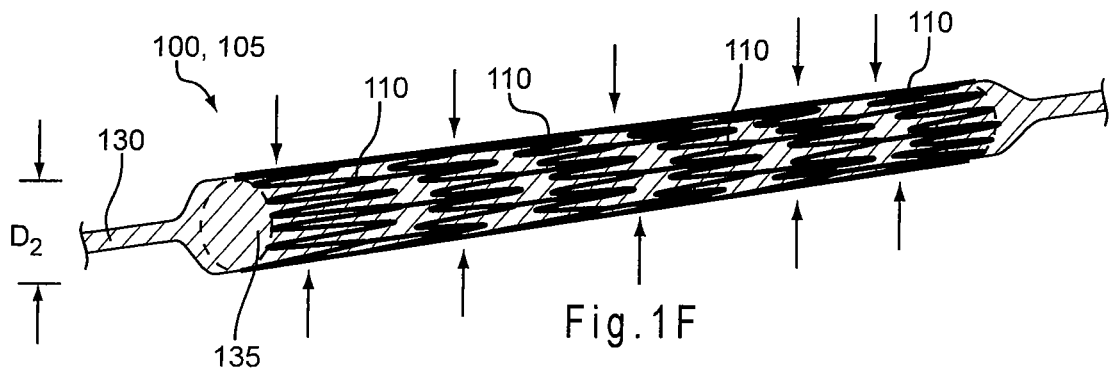
Figure 2A:
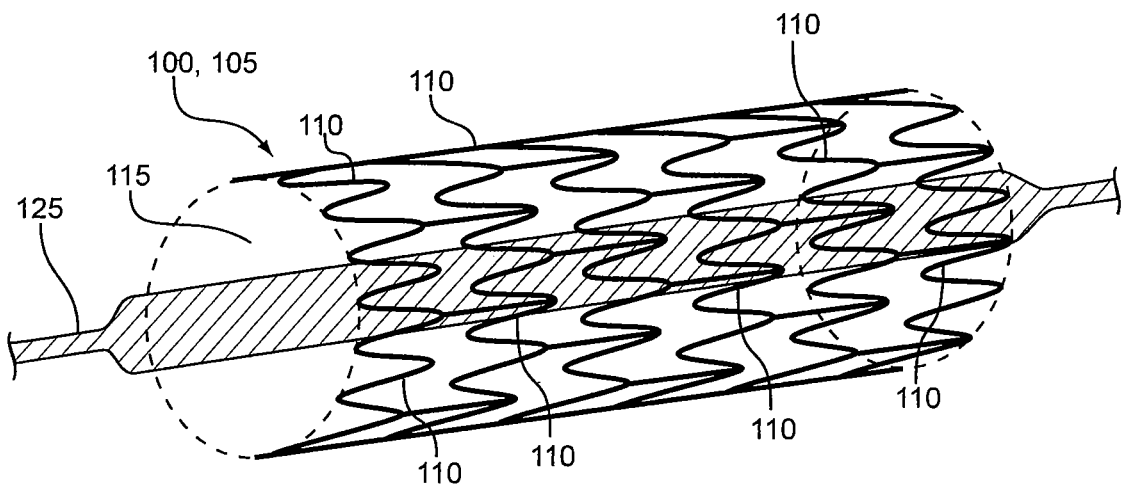
FIGS. 2A-2F show an embodiment of the method where an inflatable device is employed in the supported first stage of the method.
Figure 2B:
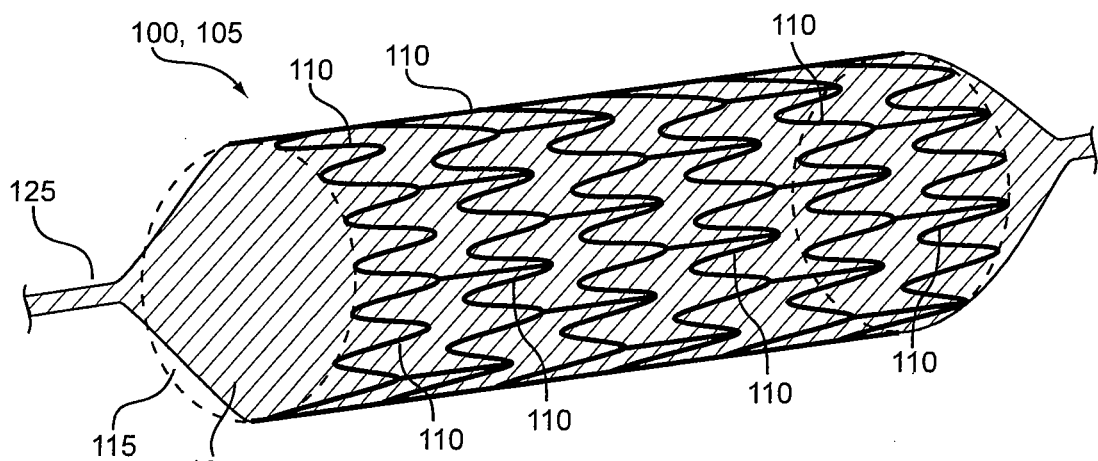
Figure 2C:
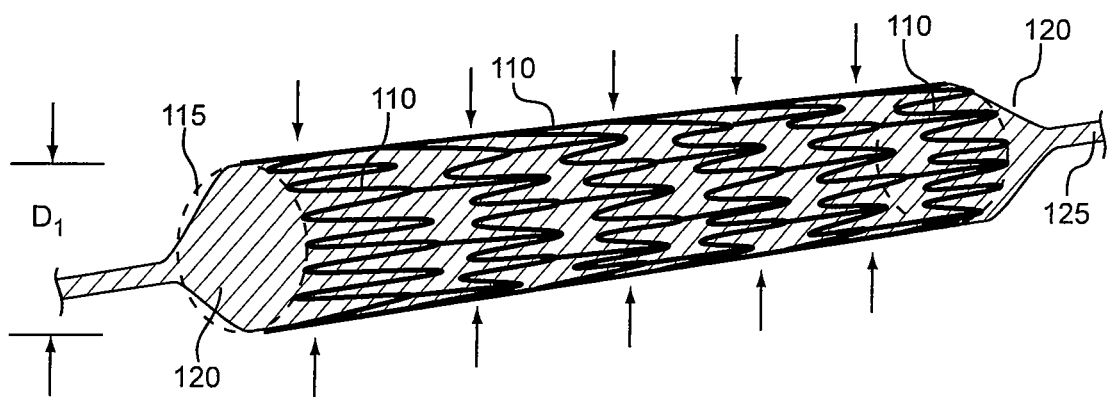

Referring again to FIG. 1A, the stent 100 may be a balloon-expandable stent in a radially expanded state prior to crimping. As shown, the stent 100 includes a thin-walled tubular framework 105 of interconnected struts 110, and the tubular framework 105 defines a lumen 115. The stent 100 may further include a coating or covering on one or more surfaces of the tubular framework 105. A radially directed outward pressure is applied to the inner surface of the tubular framework 105 to support the stent 100. The outward pressure may be applied by inflating an inflatable body 120 within the lumen 115, as shown in FIGS. 2A-2C, and as discussed further below. A diameter of the stent 100 is reduced to a first compressed diameter $D_1$ while applying the outward pressure, as shown in FIG. 1C, and then the outward pressure is stopped, as illustrated in FIG. 1D. A delivery balloon catheter 130, which includes an uninflated balloon 135 configured for delivery into a body vessel, is inserted into the lumen after halting the outward pressure, as shown in FIG. 1E. Finally, the diameter of the stent is compressed to a second compressed diameter $D_2$, which is smaller than the first compressed diameter $D_1$, to crimp the stent 100 without support onto the delivery balloon catheter 130, as shown in FIG. 1F. Further processing, such as heat setting of the balloon, may be necessary to further improve securement of the stent to the delivery balloon catheter.

Referring now to FIG. 2B, the outward pressure employed during the first stage of the crimping process may be applied to the tubular framework 105 by inflating an inflatable body 120 which is disposed within the lumen 115 of the stent 100. Preferably, the stent 100 does not expand in response to the outward pressure. The outer surface of the stent 100 may be supported to counter the outward pressure (e.g., within a crimping apparatus), as discussed further below, or the outward pressure applied to the tubular framework 105 may be insufficient to radially expand the stent 100.

Generally, the inflatable body 120 is inserted into the lumen 115 in an uninflated state and is then inflated to contact the struts 110 and provide the desired outward pressure. The shape of the inflatable body 120 is selected so that, when inflated, the inflatable body 120 contacts the inner surface of the tubular framework 105 along substantially the entire length and circumference of the stent 100. For example, the inflatable body 120 may have a cylindrical inflated shape which is sized to span the length of the balloon-expandable stent, as shown in FIG. 2B. The inflation may be carried out using a suitable inflation fluid, which may be a gas or a liquid. For example, water, saline, air, nitrogen, helium, argon, or a similar fluid may be introduced into the inflatable body to provide the desired outward pressure against the inner surface of the tubular framework 105. An outward pressure in the range of from about 1 atm to about 10 atm may be suitable for supporting the stent 100 in preparation for the first stage of the crimping process. An outward pressure of from about 7 atm to about 10 atm may also be suitable to provide the desired support. A pressure gauge and/or feedback control valve may be used to monitor and control the pressure inside the inflatable body 120.

The inflatable body 120 may be a medical balloon that is introduced into the lumen of the stent by way of a balloon catheter 125. The balloon catheter 125 is an elongate tube attached to the balloon 120 which includes an inflation lumen, or passageway, for introduction of the inflation fluid. The inflatable body 120 may have a wall thickness typical of noncompliant medical balloons in current use, such as from about 0.05 mm to about 0.07 mm. However, because the balloon catheter 125 that may be used in the first stage of the crimping process is not intended for insertion in the body (and thus does not have to satisfy strict low-profile requirements), larger wall thicknesses may also be suitable. For example, the inflatable body 120 may have a wall thickness in the range of from about 0.05 mm to about 0.1 mm. A wall thickness of greater than about 0.1 mm may also be employed for the inflatable body 120. Higher wall thicknesses may be particularly advantageous as they may allow for increased durability and reuse of the inflatable body 120. For the same reasons, a balloon catheter 125 attached to the inflatable body 120 may have a rigid instead of a flexible shaft as would be typical of current balloon catheters intended for use in the body.

Referring to FIG. 2C, the diameter of the stent 100 is reduced to a first compressed diameter $D_1$ while applying the outward pressure from the inflatable body 120. A radially directed inward force ("compression force") is applied to an outer surface of the tubular framework 105 to reduce the diameter of the stent 100. This may be done by way of a commercially available crimping tool or apparatus that encloses the stent, such as a manual or automatic crimp iris available from Machine Solutions, Inc. (Flagstaff, Ariz.). The compression force may range from about 4 lbf to about 120 lbf, depending on the size of the stent, the outward pressure, and other factors. The inward force may be maintained at a substantially constant value as the outward pressure is decreased in order to crimp the stent to the first compressed diameter $D_1$. Alternatively, the inward force may be increased to achieve the desired decrease in diameter.

The flow of the inflation fluid into or out of the inflatable body may be adjusted as the diameter of the stent is reduced to provide a variable outward pressure during the supported stage of crimping. The inward force may also be adjusted (e.g., by controlling the speed of the crimp head) to influence the outward pressure. The balancing of the outward pressure with the inward force (pressure) may be done manually or automatically. Preferably, the outward pressure is decreased as the diameter of the stent is reduced. The outward pressure may be decreased at such a rate that the pressure reaches zero after, or as, the first compressed diameter is attained. To ensure that the tubular framework of interconnected struts crimps uniformly onto the balloon, the outward pressure is maintained at some level during the entirety of the process to reach the first compressed diameter. The diameter of the stent may be reduced to the first compressed diameter at a rate of 1 mm/s.

Generally, the diameter of the stent is reduced by about 5% to about 60% during the supported stage of the crimping process to reach the first compressed diameter. The diameter may also be reduced by about 10% to about 40% during this stage, or by about 10% to about 30%. For example, the diameter of the stent prior to crimping may be an expanded diameter in the range of from about 8 mm to about 12 mm, and the first compressed diameter may lie in the range of from about 4 mm to about 9 mm. The first compressed diameter may also lie in the range of from about 6 mm to about 8 mm. The targeted first compressed diameter may depend on the size of the delivery balloon catheter over which the partially crimped stent will be positioned for the second stage of the crimping process, as well as the maximum size of the opening of a crimping apparatus that may be used for the second stage crimp. If the first compressed diameter is too small, then there may be insufficient clearance to pass the partially crimped stent over the delivery balloon catheter without snagging the balloon. If the first compressed diameter is too large, then the partially crimped stent may not fit within the desired crimping apparatus. More importantly, if the stent is not crimped down sufficiently during the first stage of the crimping method, then the stent may not compress in a stable and predictable manner during the unsupported second stage of the process.

Figure 2D:
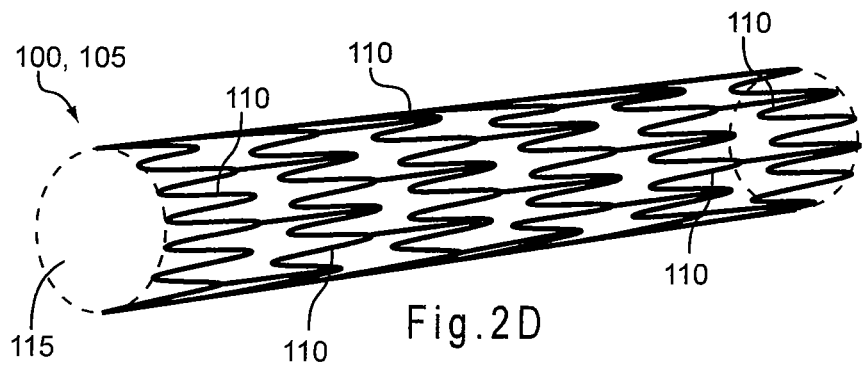

Referring to FIG. 2D, after reaching the first compressed diameter $D_1$, the outward pressure is halted. If an inflatable device such as a medical balloon has been employed to supply the outward pressure, then the device may be deflated to a point at which it is no longer contacting an inner surface of the tubular framework of the stent. The inflatable device (or other mechanism employed to supply the outer pressure) is removed from the lumen of the tubular framework of the stent. This may entail retracting a balloon catheter holding the deflated medical balloon.

Figure 2E:
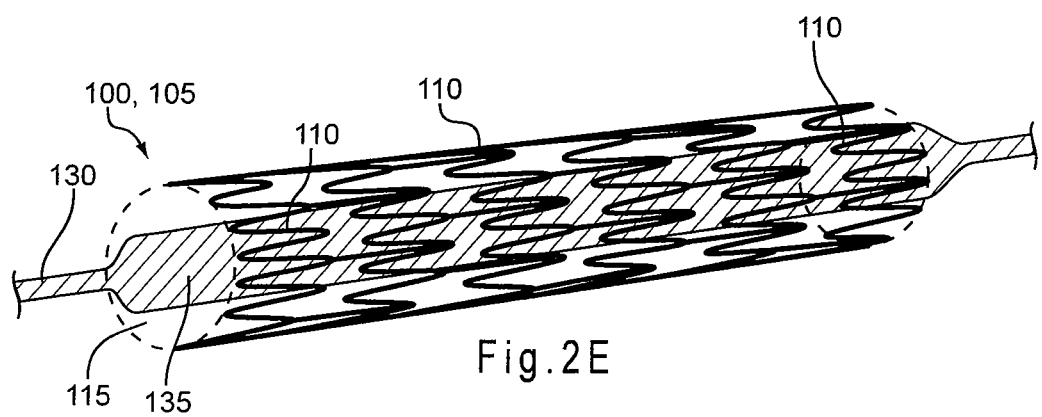

Referring to FIG. 2E, a delivery balloon catheter 130 is inserted into the lumen of the tubular framework of the stent after the inflatable device or other mechanism is removed. The delivery balloon catheter 130 supports an uninflated medical balloon 135 which is intended for use at an endoluminal treatment site. The uninflated medical balloon 135 is advantageously pleated and folded or otherwise configured for delivery into a body vessel. Once the delivery balloon catheter 130 is positioned within the lumen 115, the balloon-expandable stent 100 is ready for the unsupported second stage of crimping onto the catheter 130.

Figure 2F:
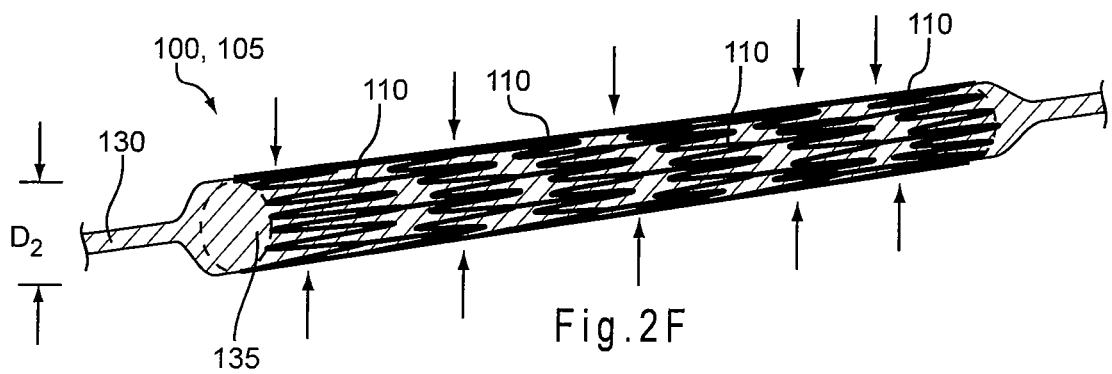

Without any underlying support, the stent 100 is crimped from the first compressed diameter $D_1$ to a second compressed diameter $D_2$, as shown in FIG. 2F. The second compressed diameter $D_2$ is smaller than the first compressed diameter $D_1$ and is suitable for securing the stent 100 to the delivery balloon catheter 130. An inward radial force (compression force) may be applied to an outer surface of the tubular framework 105 to achieve the reduction in diameter. This may be done by way of a commercially available crimping tool or apparatus, such as a manual or automatic crimp iris available from Machine Solutions, Inc. (Flagstaff, Ariz.). The compression force may range from about 1 lbf to about 300 lbf, depending on the size of the stent and other factors. Other compression forces are also possible. The supported first crimp and the unsupported second crimp may be carried out in the same crimping device or in different crimping devices.

Figure 3A:
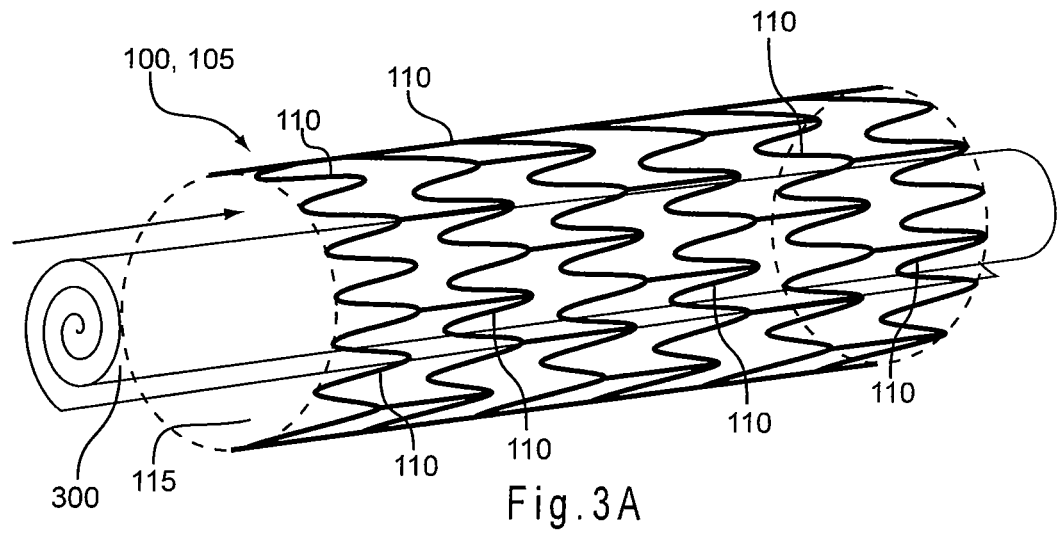
FIGS. 3A-3F show an embodiment of the method where a mechanically expandable apparatus is employed in the supported first stage of the method.
Figure 3B:
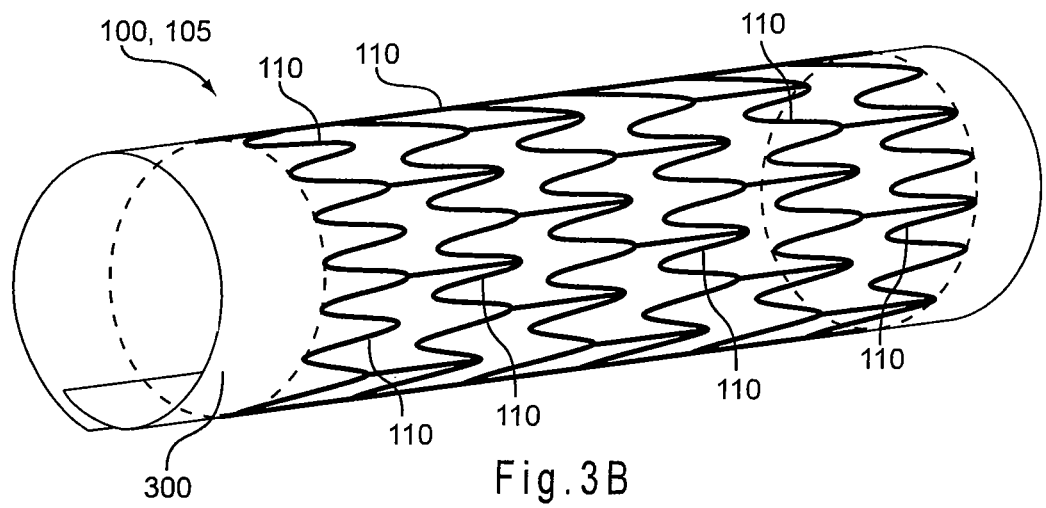
Figure 3C:
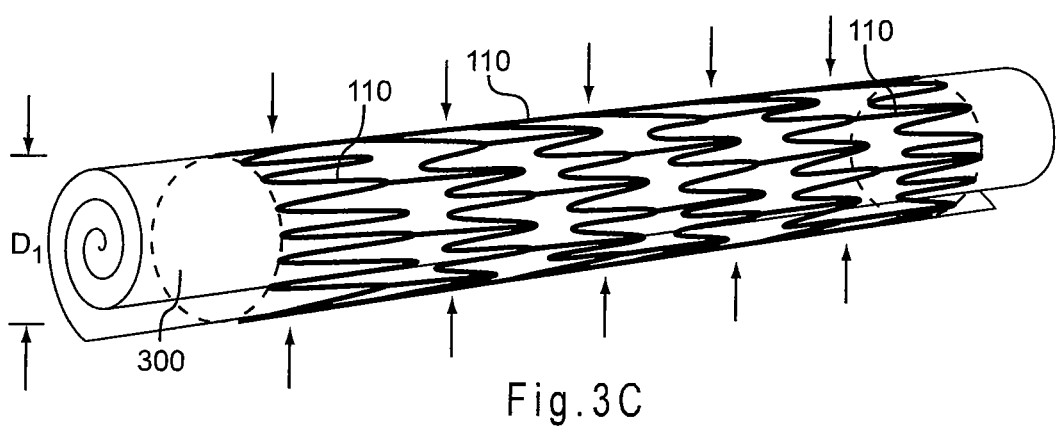
Figure 3D:
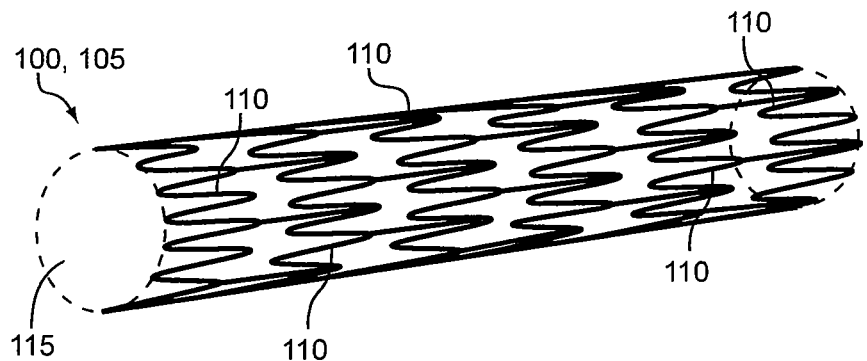
Figure 3E:
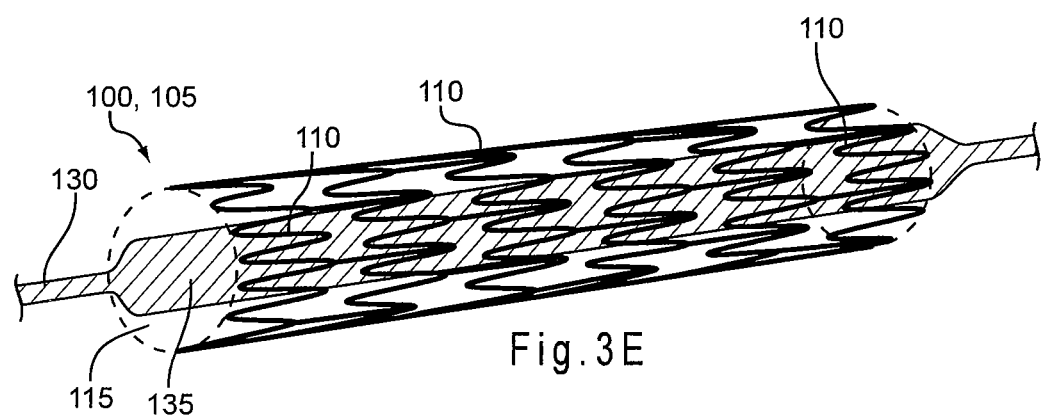
Figure 3F:
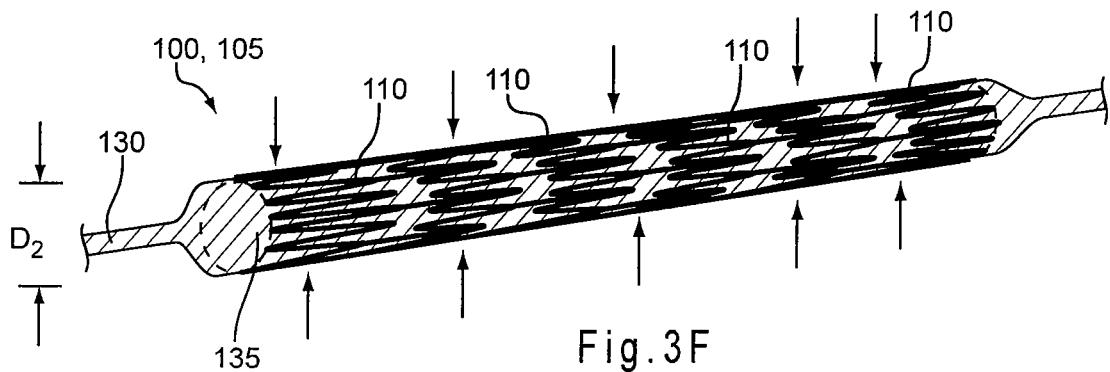

As noted above, a mechanically expandable apparatus may be used in place of the inflatable body to apply the radially directed outward pressure to support the stent during the first stage of the crimping or compression process. Referring to FIGS. 3A-3E, the mechanically expandable apparatus may take the form of a thin foil or sheet (e.g., stainless steel shim stock) 300 that is wound upon itself to form a radially expandable and contractible cylindrical shape that may be inserted into the lumen 115 of the stent 100, as shown in FIG. 3A. Because of the tendency of the foil 300 to unwind within the lumen 115, it provides a radially directed outward force against the inner surface of the tubular framework 105 before and during the compression of the stent 100, as indicated in FIGS. 3B and 3C. As the stent 100 is compressed, the foil 300 is forced to a smaller diameter configuration $D_1$ by further winding upon itself. Once the compression has proceeded sufficiently far that the stent 100 may be uniformly compressed without support, the foil 300 may be removed from the lumen 115, as indicated in FIG. 3D. If the stent 100 is a balloon-expandable stent, a delivery balloon catheter 130 including an uninflated medical balloon 135 may be inserted into the lumen 115, and the stent 100 may be further crimped without support to the desired diameter $D_2$, as shown in FIG. 3E, so as to securely engage the delivery balloon catheter 130.

In the case of a self-expanding stent, the first stage of the crimping process may be carried out as described above in reference to FIGS. 1A-1D, 2A-2D, and 3A-3D, where the stent 100 is a self-expanding stent 100 instead of the balloon-expandable stent described previously, except that the radially directed inward force may be maintained at some level after the first compressed diameter $D_1$ is reached to prevent the stent 100 from expanding prior to initiating the second stage of the compression. The second stage of the process may then be carried out as shown in FIGS. 4A-4B. Referring to FIG. 4A, once the inflatable body (or the mechanically expandable apparatus) has been removed from the lumen 115 of the stent 100, as shown in FIG. 2D (or FIG. 3D), the self-expanding stent 100 may be radially compressed without support to a desired compressed diameter $D_2$. Then, the stent 100 may be inserted into a delivery device (e.g., transfer tube, sheath or other tubular restraining member) 400 without removing the compression force in preparation for delivery into a body vessel.

Figure 5:
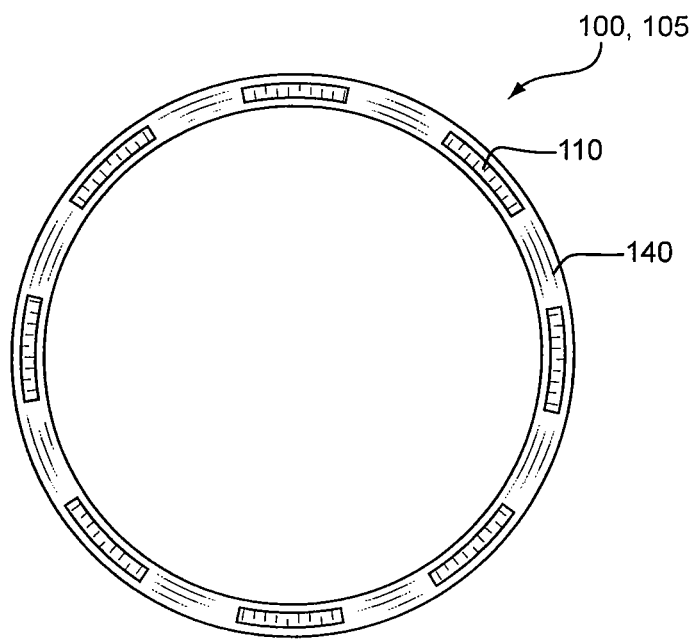
FIG. 5 shows a cross-sectional schematic of an expandable stent that includes a coating or covering.

The expandable stent used in the two-stage crimping process may be a covered balloon-expandable stent that has undergone a preliminary expansion process for application of a covering to one or more surfaces of the struts, as noted above. An exemplary stent covering process is described in more detail in U.S. Patent Application No. 2008/0195193 "Covered Balloon Expandable Stent Design and Method of Covering," which is hereby incorporated by reference in its entirety. The tubular framework 105 of the balloon-expandable stent 100 may thus include a covering or coating 140, as shown in the cross-sectional schematic of FIG. 5. The coating 140 may be formed of a biocompatible polymer, such as Thoralon (Thoratec, Inc., Pleasanton, Calif.), which is a blend of segmented polyetherurethane urea and a siloxane containing a surface-modifying additive (SMA). Other materials, such as other biocompatible polymers, metals or alloys, may also be suitable for the coating 140.

The thin-walled tubular framework 105 of interconnected struts 110 may be fabricated from a thin-walled tube or cannula that has been laser-cut to selectively remove portions of the tube, leaving a desired pattern of struts. For example, the tubular framework may include substantially straight segments linked by bent segments that form a serpentine pattern of interconnected struts about the circumference. An exemplary stent including a serpentine pattern of interconnected struts is the Formula™ balloon-expandable stent of Cook, Inc. (Bloomington, Ind.). Any strut pattern that may be laser-cut or otherwise carved out of a thin-walled tube may be suitable for the tubular framework, provided that the stent provides sufficient radial support when expanded at the endoluminal treatment site. The tubular framework may alternatively be composed of a cylindrical woven wire structure or another configuration based on one or more interlaced wires. Typically, in the case of balloon-expandable stents, the framework of the stent is formed from a strong but ductile biocompatible metal alloy, such as stainless steel or a cobalt-chromium alloy. Self-expanding stents may have a framework formed from a nickel-titanium alloy that behaves superelastically at body temperature. Such alloys are commonly referred to as Nitinol alloys.

The radially expanded state in which the stent may be provided for the first stage of the crimping process is attained by deforming the as-fabricated stent framework into a larger-diameter configuration. The radially expanded state may correspond to the maximum expanded diameter of the stent, where the maximum expanded diameter corresponds to the largest diameter at which the stent is designed to be used. Alternatively, the radially expanded state may correspond to some fraction of the maximum expanded diameter, such as about 90% of the maximum expanded diameter or greater, or about 80% of the maximum expanded diameter or greater. To deform the stent to the expanded state, the stent may be disposed over a tapered mandrel having an increasing diameter along its length, and then moved along the length of the mandrel to achieve the desired radial dimensions. Other expansion methods known in the art, such as using a medical balloon catheter, may also be used. It is also envisioned that the stent may be cut from tubing with an outside diameter equivalent to the maximum expanded diameter of the stent, or some fraction of that diameter, and thus no deformation of the as-cut stent framework may be needed to provide the stent in the radially expanded state prior to crimping.

Example

A covered balloon-expandable stent of approximately 10 mm in nominal (expanded) diameter and 60 mm in length (10×60) is crimped down to approximately 3 mm in diameter for attachment to a balloon catheter. When the crimping process is carried out without supporting the stent (i.e., without providing an outward pressure against the inner surface of the tubular framework), the struts of the end cells become nonparallel and do not lay uniformly on the surface of the balloon.

When the improved crimping process is employed to crimp the 10×60 covered stent, instabilities that cause misalignments and misorientations of the struts can be avoided. In this example, the 10×60 covered stent is placed over a 10×60 balloon catheter, and the latter is inflated to 8 atm by infusing saline fluid. At this pressure, the balloon lays snugly against the inner surface of the tubular framework of the expanded covered stent. The inflated balloon catheter and overlying covered stent are transferred into a manual crimp iris produced by Machine Solutions, Inc. (Flagstaff, Ariz.) The crimp iris is closed until the balloon inflation pressure increases to approximately 9 atm.

The force of closure on the iris (approximately 100 lbf) is maintained as the inflation pressure in the balloon is lowered by manually removing saline fluid, and the covered stent is reduced in diameter. The process is continued until the iris has reached the set point of about 6.3 mm, corresponding to the first compressed diameter ($D_1$). At this point, the pressure in the balloon is lowered to zero and the balloon catheter is removed. This amount of pre-crimp is found to be sufficient for the struts to crimp uniformly during the final crimp to the second compressed diameter, which is done without an underlying support. At this point, the covered stent is placed over a final balloon catheter, which has been folded to an outer diameter of approximately 2 mm. The covered stent is placed in a servo-controlled, automatic crimping apparatus produced by Machine Solutions, Inc. and is crimped to the second compressed diameter ($D_2$) without support.

Covered balloon-expandable stents, particularly stents that are crimped by the improved method described here, may be used to treat aneurysms in vessels such as the iliac, internal iliac, and renal arteries. They may also be used for fenestrations, where the covering is important to prevent leakage. Using the improved crimping method, such stents may be crimped from a radially expanded state onto a balloon catheter for delivery into the body without the instabilities that may occur during traditional unsupported crimping processes. Self-expanding stents, which are widely used to treat blockages and other narrowing ailments in peripheral vessels, may also be more uniformly compressed to a delivery configuration using the two-stage compression method described herein.

Although the present invention has been described in considerable detail with reference to certain embodiments thereof, other embodiments are possible without departing from the present invention. The spirit and scope of the appended claims should not be limited, therefore, to the description of the preferred embodiments included here. All embodiments that come within the meaning of the claims, either literally or by equivalence, are intended to be embraced therein. Furthermore, the advantages described above are not necessarily the only advantages of the invention, and it is not necessarily expected that all of the described advantages will be achieved with every embodiment of the invention.

The invention claimed is:

1. A method of crimping a balloon-expandable stent in preparation for delivery into a body vessel, comprising:
   providing a balloon-expandable stent comprising a thin-walled tubular framework of interconnected struts, the tubular framework defining a lumen;
   inserting a mechanically expandable apparatus into the lumen, the mechanically expandable apparatus comprising a sheet wound upon itself to form a radially expandable and contractible cylindrical shape, the sheet unwinding within the lumen to provide an outward pressure against an inner surface of the tubular framework to support the stent;
   reducing a diameter of the stent to a first compressed diameter while applying the outward pressure, the sheet further winding upon itself to a smaller diameter configuration as the diameter of the stent is reduced;
   halting the outward pressure after reaching the first compressed diameter;
   removing the mechanically expandable apparatus from the lumen;

inserting a delivery balloon catheter into the lumen after halting the outward pressure and removing the mechanically expandable apparatus, the delivery balloon catheter comprising an uninflated balloon in a delivery configuration; and reducing the diameter of the stent to a second compressed diameter smaller than the first compressed diameter to crimp the stent onto the delivery balloon catheter.

2. The method of claim 1, including providing the balloon-expandable stent in a radially expanded state.

3. The method of claim 1, where the outward pressure is in the range of from about 7 atm to about 10 atm prior to reducing the diameter of the stent to the first compressed diameter.

4. The method of claim 1, where the outward pressure is insufficient to radially expand the stent.

5. The method of claim 1, where a radially directed inward force applied to an outer surface of the tubular framework counters the outward pressure.

6. The method of claim 1, where the outward pressure is a variable outward pressure.

7. The method of claim 6, further comprising decreasing the outward pressure as the diameter of the stent is reduced to the first compressed diameter.

8. The method of claim 1, further comprising applying a radially directed inward force in the range of from about 4 lbf to about 120 lbf to an outer surface of the tubular framework to reduce the diameter of the stent to the first compressed diameter.

9. The method of claim 1, further comprising inserting the stent into a first crimping apparatus to reduce the diameter of the stent to at least one of the first compressed diameter and the second compressed diameter.

10. The method of claim 9, further comprising inserting the stent into a second crimping apparatus to reduce the diameter of the stent to the second compressed diameter.

11. The method of claim 1, where the first compressed diameter is from about 10% to about 30% smaller than a starting diameter of the stent.

12. The method of claim 1, where the first compressed diameter is from about 6 mm to about 8 mm.

13. The method of claim 1, where the balloon-expandable stent is a covered stent comprising a polymeric coating.

14. The method of claim 1, where the balloon-expandable stent is provided in a radially expanded state, the balloon-expandable stent being a covered stent comprising a polymeric coating, and where the first compressed diameter is from about 10% to about 30% smaller than a starting diameter of the stent.

15. The method of claim 14, further comprising inserting the stent into a crimping apparatus to reduce the diameter of the stent to at least one of the first compressed diameter and the second compressed diameter, where reducing the diameter of the stent to the first compressed diameter comprises applying a radially directed inward force in the range of from about 4 lbf to about 120 lbf to an outer surface of the tubular framework.

16. A method of compressing a self-expanding stent in preparation for delivery into a body vessel, comprising:

providing a self-expanding stent comprising a thin-walled tubular framework of interconnected struts, the tubular framework defining a lumen;

inserting a mechanically expandable apparatus into the lumen, the mechanically expandable apparatus comprising a sheet wound upon itself to form a radially expandable and contractible cylindrical shape, the sheet unwinding within the lumen to provide an outward pressure against an inner surface of the tubular framework to support the stent;

reducing a diameter of the stent to a first compressed diameter while applying the outward pressure, the sheet further winding upon itself to a smaller diameter configuration as the diameter of the stent is reduced;

halting the outward pressure after reaching the first compressed diameter;

removing the mechanically expandable apparatus from the lumen;

reducing the diameter of the stent to a second compressed diameter smaller than the first compressed diameter; and transferring the stent into a restraining member sized to receive the stent having the second compressed diameter.

* * * * *